US012558164B2

(12) United States Patent
Frushour

(10) Patent No.: US 12,558,164 B2
(45) Date of Patent: Feb. 24, 2026

(54) CREATING A NAVIGATION PATHWAY TO A TARGET IN THE LUNG AND METHOD OF NAVIGATING TO THE TARGET

(71) Applicant: Covidien LP, Mansfield, MA (US)

(72) Inventor: Scott E.M. Frushour, Boulder, CO (US)

(73) Assignee: Covidien LP, Mansfield, MA (US)

( * ) Notice: Subject to any disclaimer, the term of this patent is extended or adjusted under 35 U.S.C. 154(b) by 537 days.

(21) Appl. No.: 17/826,565

(22) Filed: May 27, 2022

(65) Prior Publication Data

US 2023/0404670 A1 Dec. 21, 2023

(51) Int. Cl.
*A61B 34/20* (2016.01)
*A61B 1/00* (2006.01)
(Continued)

(52) U.S. Cl.
CPC .......... *A61B 34/10* (2016.02); *A61B 1/00045* (2013.01); *A61B 1/05* (2013.01); *A61B 2034/107* (2016.02); *A61B 2034/2055* (2016.02); *A61B 2034/2065* (2016.02); *A61B 2034/303* (2016.02)

(58) Field of Classification Search
USPC ......... 128/897–899, 920, 922–925; 382/103, 382/128–133, 153–157
See application file for complete search history.

(56) References Cited

U.S. PATENT DOCUMENTS

| | | | |
|---|---|---|---|
| 8,335,359 | B2 | 12/2012 | Fidrich et al. |
| 8,706,184 | B2 | 4/2014 | Mohr et al. |
| 8,827,934 | B2 | 9/2014 | Chopra et al. |
| 9,918,659 | B2 | 3/2018 | Chopra et al. |

(Continued)

FOREIGN PATENT DOCUMENTS

| | | |
|---|---|---|
| BR | 0013237 A | 7/2003 |
| BR | 0116004 A | 6/2004 |

(Continued)

OTHER PUBLICATIONS

Ummalaneni Ritwik; Robotic Systems for Determining a Pose of a Medical Device in Luminal Networks; 2018 (Year: 2018).*

(Continued)

*Primary Examiner* — Marcellus J Augustin
(74) *Attorney, Agent, or Firm* — Weber Rosselli & Cannon LLP

(57) ABSTRACT

A system for performing a surgical procedure includes a controller including a memory and a processor, the memory storing instructions, which when executed by the processor cause the processor to receive a plurality of pre-procedure images of a patient's anatomy, label anatomical structures within at least a portion of the pre-procedure images, generate a three-dimensional reconstruction of the patient's anatomy using the plurality of pre-procedure images, receive an image captured by the camera, identify anatomical structures within the image captured by the camera to labeled anatomical structures within the plurality of pre-procedure images, identify an image from the plurality of pre-procedure images that corresponds to the image captured by the camera, and register the location where the image was captured by the camera to the three-dimensional reconstruction of the patient's anatomy.

20 Claims, 9 Drawing Sheets

(51) Int. Cl.

| | | |
|---|---|---|
| *A61B 1/05* | (2006.01) |
| *A61B 34/10* | (2016.01) |
| *A61B 34/30* | (2016.01) |
| *G06T 5/00* | (2024.01) |
| *G06T 5/60* | (2024.01) |
| *G06T 7/30* | (2017.01) |

(56) References Cited

U.S. PATENT DOCUMENTS

| | | | |
|---|---|---|---|
| 10,373,719 | B2 | 8/2019 | Soper et al. |
| 10,376,178 | B2 | 8/2019 | Chopra |
| 10,405,753 | B2 | 9/2019 | Sorger |
| 10,478,162 | B2 | 11/2019 | Barbagli et al. |
| 10,480,926 | B2 | 11/2019 | Froggatt et al. |
| 10,524,866 | B2 | 1/2020 | Srinivasan et al. |
| 10,555,788 | B2 | 2/2020 | Panescu et al. |
| 10,610,306 | B2 | 4/2020 | Chopra |
| 10,638,953 | B2 | 5/2020 | Duindam et al. |
| 10,674,970 | B2 | 6/2020 | Averbuch et al. |
| 10,682,070 | B2 | 6/2020 | Duindam |
| 10,706,543 | B2 | 7/2020 | Donhowe et al. |
| 10,709,506 | B2 | 7/2020 | Coste-Maniere et al. |
| 10,772,485 | B2 | 9/2020 | Schlesinger et al. |
| 10,796,432 | B2 | 10/2020 | Mintz et al. |
| 10,823,627 | B2 | 11/2020 | Sanborn et al. |
| 10,827,913 | B2 | 11/2020 | Ummalaneni et al. |
| 10,835,153 | B2 | 11/2020 | Rafii-Tari et al. |
| 10,885,630 | B2 | 1/2021 | Li et al. |
| 2003/0013972 | A1 | 1/2003 | Makin |
| 2008/0188962 | A1* | 8/2008 | Suryanarayanan .. G06V 10/457 |
| | | | 700/89 |
| 2013/0303945 | A1 | 11/2013 | Blumenkranz et al. |
| 2014/0035798 | A1 | 2/2014 | Kawada et al. |
| 2015/0148690 | A1 | 5/2015 | Chopra et al. |
| 2015/0265368 | A1 | 9/2015 | Chopra et al. |
| 2016/0157939 | A1 | 6/2016 | Larkin et al. |
| 2016/0183841 | A1 | 6/2016 | Duindam et al. |
| 2016/0192860 | A1 | 7/2016 | Allenby et al. |
| 2016/0287344 | A1 | 10/2016 | Donhowe et al. |
| 2017/0112576 | A1 | 4/2017 | Coste-Maniere et al. |
| 2017/0140532 | A1* | 5/2017 | Dascal ..................... G06T 5/50 |
| 2017/0161455 | A1* | 6/2017 | Grady .................. G16H 10/60 |
| 2017/0209071 | A1 | 7/2017 | Zhao et al. |
| 2017/0265952 | A1 | 9/2017 | Donhowe et al. |
| 2017/0311844 | A1 | 11/2017 | Zhao et al. |
| 2017/0319165 | A1 | 11/2017 | Averbuch |
| 2018/0078318 | A1 | 3/2018 | Barbagli et al. |
| 2018/0153621 | A1 | 6/2018 | Duindam et al. |
| 2018/0235709 | A1 | 8/2018 | Donhowe et al. |
| 2018/0240237 | A1 | 8/2018 | Donhowe et al. |
| 2018/0256262 | A1 | 9/2018 | Duindam et al. |
| 2018/0263706 | A1 | 9/2018 | Averbuch |
| 2018/0279852 | A1 | 10/2018 | Rafii-Tari et al. |
| 2018/0325419 | A1 | 11/2018 | Zhao et al. |
| 2019/0000559 | A1 | 1/2019 | Berman et al. |
| 2019/0000560 | A1 | 1/2019 | Berman et al. |
| 2019/0008413 | A1 | 1/2019 | Duindam et al. |
| 2019/0038365 | A1 | 2/2019 | Soper et al. |
| 2019/0065209 | A1 | 2/2019 | Mishra et al. |
| 2019/0110839 | A1 | 4/2019 | Rafii-Tari et al. |
| 2019/0175062 | A1 | 6/2019 | Rafii-Tari et al. |
| 2019/0180500 | A1* | 6/2019 | Shen ...................... G06T 17/00 |
| 2019/0183318 | A1 | 6/2019 | Froggatt et al. |
| 2019/0183585 | A1 | 6/2019 | Rafii-Tari et al. |
| 2019/0183587 | A1 | 6/2019 | Rafii-Tari et al. |
| 2019/0192234 | A1 | 6/2019 | Gadda et al. |
| 2019/0209016 | A1 | 7/2019 | Herzlinger et al. |
| 2019/0209043 | A1 | 7/2019 | Zhao et al. |
| 2019/0216548 | A1 | 7/2019 | Ummalaneni |
| 2019/0239723 | A1 | 8/2019 | Duindam et al. |
| 2019/0239831 | A1 | 8/2019 | Chopra |
| 2019/0250050 | A1 | 8/2019 | Sanborn et al. |
| 2019/0254649 | A1 | 8/2019 | Walters et al. |
| 2019/0269470 | A1 | 9/2019 | Barbagli et al. |
| 2019/0272634 | A1 | 9/2019 | Li et al. |

| | | | |
|---|---|---|---|
| 2019/0298160 | A1 | 10/2019 | Ummalaneni et al. |
| 2019/0298451 | A1 | 10/2019 | Wong et al. |
| 2019/0320878 | A1 | 10/2019 | Duindam et al. |
| 2019/0320937 | A1 | 10/2019 | Duindam et al. |
| 2019/0336238 | A1 | 11/2019 | Yu et al. |
| 2019/0343424 | A1 | 11/2019 | Blumenkranz et al. |
| 2019/0350659 | A1 | 11/2019 | Wang et al. |
| 2019/0365199 | A1 | 12/2019 | Zhao et al. |
| 2019/0365479 | A1 | 12/2019 | Rafii-Tari |
| 2019/0365486 | A1 | 12/2019 | Srinivasan et al. |
| 2019/0380787 | A1 | 12/2019 | Ye et al. |
| 2020/0000319 | A1 | 1/2020 | Saadat et al. |
| 2020/0000526 | A1 | 1/2020 | Zhao |
| 2020/0008655 | A1 | 1/2020 | Schlesinger et al. |
| 2020/0030044 | A1 | 1/2020 | Wang et al. |
| 2020/0030461 | A1 | 1/2020 | Sorger |
| 2020/0038750 | A1 | 2/2020 | Kojima |
| 2020/0043207 | A1 | 2/2020 | Lo et al. |
| 2020/0046431 | A1 | 2/2020 | Soper et al. |
| 2020/0046436 | A1 | 2/2020 | Tzeisler et al. |
| 2020/0054399 | A1 | 2/2020 | Duindam et al. |
| 2020/0060771 | A1 | 2/2020 | Lo et al. |
| 2020/0069192 | A1 | 3/2020 | Sanborn et al. |
| 2020/0077870 | A1 | 3/2020 | Dicarlo et al. |
| 2020/0078095 | A1 | 3/2020 | Chopra et al. |
| 2020/0078103 | A1 | 3/2020 | Duindam et al. |
| 2020/0085514 | A1 | 3/2020 | Blumenkranz |
| 2020/0109124 | A1 | 4/2020 | Pomper et al. |
| 2020/0129045 | A1 | 4/2020 | Prisco |
| 2020/0129239 | A1 | 4/2020 | Bianchi et al. |
| 2020/0138515 | A1 | 5/2020 | Wong |
| 2020/0155116 | A1 | 5/2020 | Donhowe et al. |
| 2020/0170623 | A1 | 6/2020 | Averbuch |
| 2020/0170720 | A1 | 6/2020 | Ummalaneni |
| 2020/0179058 | A1 | 6/2020 | Barbagli et al. |
| 2020/0188038 | A1 | 6/2020 | Donhowe et al. |
| 2020/0205903 | A1 | 7/2020 | Srinivasan et al. |
| 2020/0205904 | A1 | 7/2020 | Chopra |
| 2020/0214664 | A1 | 7/2020 | Zhao et al. |
| 2020/0229679 | A1 | 7/2020 | Zhao et al. |
| 2020/0242767 | A1 | 7/2020 | Zhao et al. |
| 2020/0275860 | A1 | 9/2020 | Duindam |
| 2020/0297442 | A1 | 9/2020 | Adebar et al. |
| 2020/0315554 | A1 | 10/2020 | Averbuch et al. |
| 2020/0330795 | A1 | 10/2020 | Sawant et al. |
| 2020/0352427 | A1 | 11/2020 | Deyanov |
| 2020/0364865 | A1 | 11/2020 | Donhowe et al. |
| 2021/0221455 | A1* | 7/2021 | Wang ................... B62D 57/032 |
| 2023/0145909 | A1* | 5/2023 | Kaplan ................... A61B 90/37 |
| | | | 600/424 |
| 2023/0281841 | A1* | 9/2023 | Soper ..................... A61B 34/35 |
| | | | 382/128 |
| 2024/0180634 | A1* | 6/2024 | Mikus ................... A61B 90/50 |

FOREIGN PATENT DOCUMENTS

| | | |
|---|---|---|
| CZ | 486540 B1 | 9/2016 |
| CZ | 2709512 B6 | 8/2017 |
| CZ | 2884879 B1 | 1/2020 |
| EP | 2918218 A1 | 9/2015 |
| EP | 3413830 A4 | 9/2019 |
| EP | 3478161 A4 | 2/2020 |
| EP | 3641686 A2 | 4/2020 |
| EP | 3644885 A1 | 5/2020 |
| EP | 3644886 A1 | 5/2020 |
| MX | PA03005028 A | 1/2004 |
| MX | 225663 B | 1/2005 |
| MX | 226292 B | 2/2005 |
| MX | 246862 B | 6/2007 |
| MX | 265247 B | 3/2009 |
| MX | 284569 B | 3/2011 |
| WO | 2014058838 A1 | 4/2014 |
| WO | 2018236587 A1 | 12/2018 |

OTHER PUBLICATIONS

Donhowe Caitlin Q; Methods for Interventional Procedure Planning; 2018 (Year: 2018).*

(56) References Cited

OTHER PUBLICATIONS

PCT Search Report and Written Opinion issued in PCT Application
No. PCT/IB2023/055261 dated Sep. 12, 2023.

* cited by examiner

CREATING A NAVIGATION PATHWAY TO A TARGET IN THE LUNG AND METHOD OF NAVIGATING TO THE TARGET

BACKGROUND

Technical Field

The present disclosure relates to the field of navigation of medical devices within a patient, and in particular, planning a pathway through a luminal network of a patient and navigating medical devices to a target.

Description of Related Art

There are several commonly applied medical methods, such as endoscopic procedures or minimally invasive procedures, for treating various maladies affecting organs including the liver, brain, heart, lungs, gall bladder, kidneys, and bones. Often, one or more imaging modalities, such as magnetic resonance imaging (MM), ultrasound imaging, computed tomography (CT), cone-beam computed tomography (CBCT) or fluoroscopy (including 3D fluoroscopy) are employed by clinicians to identify and navigate to areas of interest within a patient and ultimately a target for biopsy or treatment. In some procedures, pre-operative scans may be utilized for target identification and intraoperative guidance. However, real-time imaging may be required to obtain a more accurate and current image of the target area. Furthermore, real-time image data displaying the current location of a medical device with respect to the target and its surroundings may be needed to navigate the medical device to the target in a safe and accurate manner (e.g., without causing damage to other organs or tissue).

For example, an endoscopic approach has proven useful in navigating to areas of interest within a patient. To enable the endoscopic approach endoscopic navigation systems have been developed that use previously acquired Mill data or CT image data to generate a three-dimensional (3D) rendering, model, or volume of the particular body part such as the lungs.

In some applications, the acquired Mill data or CT Image data may be acquired during the procedure (perioperatively). The resulting volume generated from the Mill scan or CT scan is then utilized to create a navigation plan to facilitate the advancement of the endoscope (or other suitable medical device) within the patient anatomy to an area of interest. In some cases, the volume generated may be used to update a previously created navigation plan. A locating or tracking system, such as an electromagnetic (EM) tracking system, or fiber-optic shape sensing system may be utilized in conjunction with, for example, CT data, to facilitate guidance of the endoscope to the area of interest.

However, CT-to-body divergence can cause inaccuracies in navigation using locating or tracking systems, leading to the use of fluoroscopic navigation to identify a current position of the medical device and correcting the location of the medical device in the 3D model. As can be appreciated, these inaccuracies can lead to increased surgical times to correct the real-time position of the medical device within the 3D models and the use of fluoroscopy leads to additional set-up time and radiation exposure.

SUMMARY

In accordance with the present disclosure, a system for performing a surgical procedure includes a controller operably coupled to a camera, the controller including a memory and a processor, the memory storing instructions, which when executed by the processor, cause the processor to receive a plurality of pre-procedure images of a patient's anatomy, label anatomical structures within at least a portion of the pre-procedure images, generate a three-dimensional reconstruction of the patient's anatomy using the plurality of pre-procedure images, receive an image captured by the camera, identify anatomical structures within the image captured by the camera, compare the identified anatomical structures within the image captured by the camera to labeled anatomical structures within the plurality of pre-procedure images, identify an image from the plurality of pre-procedure images that corresponds to the image captured by the camera, and register the location where the image was captured by the camera to the three-dimensional reconstruction of the patient's anatomy.

In aspects, the system may include a surgical device, wherein the camera is disposed on a distal portion of the surgical device, wherein the surgical device is navigable within a portion of the patient's anatomy.

In certain aspects, the instructions, when executed by the processor, may cause the processor to generate a pathway to a target tissue.

In other aspects, the instructions, when executed by the processor, may cause the processor to label anatomical structures adjacent the pathway to the target tissue.

In certain aspects, the instruction, when executed by the processor, may cause the processor to confirm that the images captured by the camera were captured from a location within the patient's anatomy that corresponds to the pathway to the target tissue.

In aspects, the instructions, when executed by the processor, may cause the processor to issue a warning if the images captured by the camera were captured from a location within the patient's anatomy that does not correspond to the pathway to the target tissue.

In other aspects, the instructions, when executed by the processor, may cause the processor to continuously receive images from the camera and continuously register the images captured by the camera to the three-dimensional reconstruction of the patient's anatomy as the surgical device is navigated through the patient's anatomy.

In certain aspects, the anatomical structures may be branches or branch points of airways within a patient's lungs.

In other aspects, the instructions, when executed by the processor, may cause the processor to label the branches or branch points within the plurality of the pre-procedure images according to a location where the branches or branch points exits within the patient's airways.

In accordance with another aspect of the present disclosure, a system for performing a surgical procedure includes an endoscope including a camera, the camera disposed on a distal portion of the endoscope, and a controller operably coupled to a camera, the controller including a memory and a processor, the memory storing instructions, which when executed by the processor cause the processor to generate a three-dimensional reconstruction of a patient's anatomy from pre-procedure images of the patient's anatomy, generate a pathway to a target tissue within the patient's anatomy, label anatomical structures adjacent the pathway to the target tissue, receive an image captured by the camera, identify anatomical structures within the image captured by the camera, compare the identified anatomical structures within the image captured by the camera to the labeled anatomical structures within the three-dimensional reconstruction of the patient's anatomy, identify a location within the three-dimensional reconstruction of the patient's anatomy that corresponds to the image captured by the camera, and register the location where the image was captured by the camera to the three-dimensional reconstruction of the patient's anatomy.

In aspects, the instructions, when executed by the processor, may cause the processor to confirm that the image captured by the camera was captured from a location within the patient's anatomy that corresponds to the pathway to the target tissue.

In certain aspects, the instructions, when executed by the processor, may cause the processor to issue a warning that the image captured by the camera was captured from a location within the patient's anatomy that does not correspond to the pathway to the target tissue.

In other aspects, the instructions, when executed by the processor, may cause the processor to continuously receive images captured by the camera and continuously register the images captured by the camera to the three-dimensional reconstruction of the patient's anatomy as the endoscope is navigated through the patient's anatomy.

In aspects, the anatomical structures may be branches or branch points of airways within the patient's lungs.

In accordance with another aspect of the present disclosure, a method of performing a surgical procedure includes receiving a plurality of pre-procedure images of a patient's anatomy, labeling anatomical structures within at least a portion of the pre-procedure images, generating a three-dimensional reconstruction of the patient's anatomy using the plurality of pre-procedure images, receiving an image captured by the camera, identifying anatomical structures within the image captured by the camera, comprising the identified anatomical structures within the image captured by the camera to labeled anatomical structures within the plurality pre-procedure images, identifying an image from the plurality of pre-procedure images that corresponds to the image captured by the camera, and registering the location where the image was captured by the camera to the three-dimensional reconstruction of the patient's anatomy.

In aspects, wherein receiving the image captured by the camera may include receiving images captured by the camera disposed on a distal portion of a surgical device, wherein the surgical device is navigable within a portion of the patient's anatomy.

In other aspects, the method may include generating a pathway to a target tissue located within the patient's anatomy.

In certain aspects, the method may include labeling anatomical structures adjacent the pathway to the target tissue.

In other aspects, the method may include confirming that the images captured by the camera were captured from a location within the patient's anatomy that corresponds to the pathway to the target tissue.

In aspects, the method may include issuing a warning if the images captured by the camera were captured from a location within the patient's anatomy that does not correspond to the pathway to the target tissue.

BRIEF DESCRIPTION OF THE DRAWINGS

Various aspects and embodiments of the disclosure are described hereinbelow with references to the drawings, wherein.

DETAILED DESCRIPTION

Figure 1:
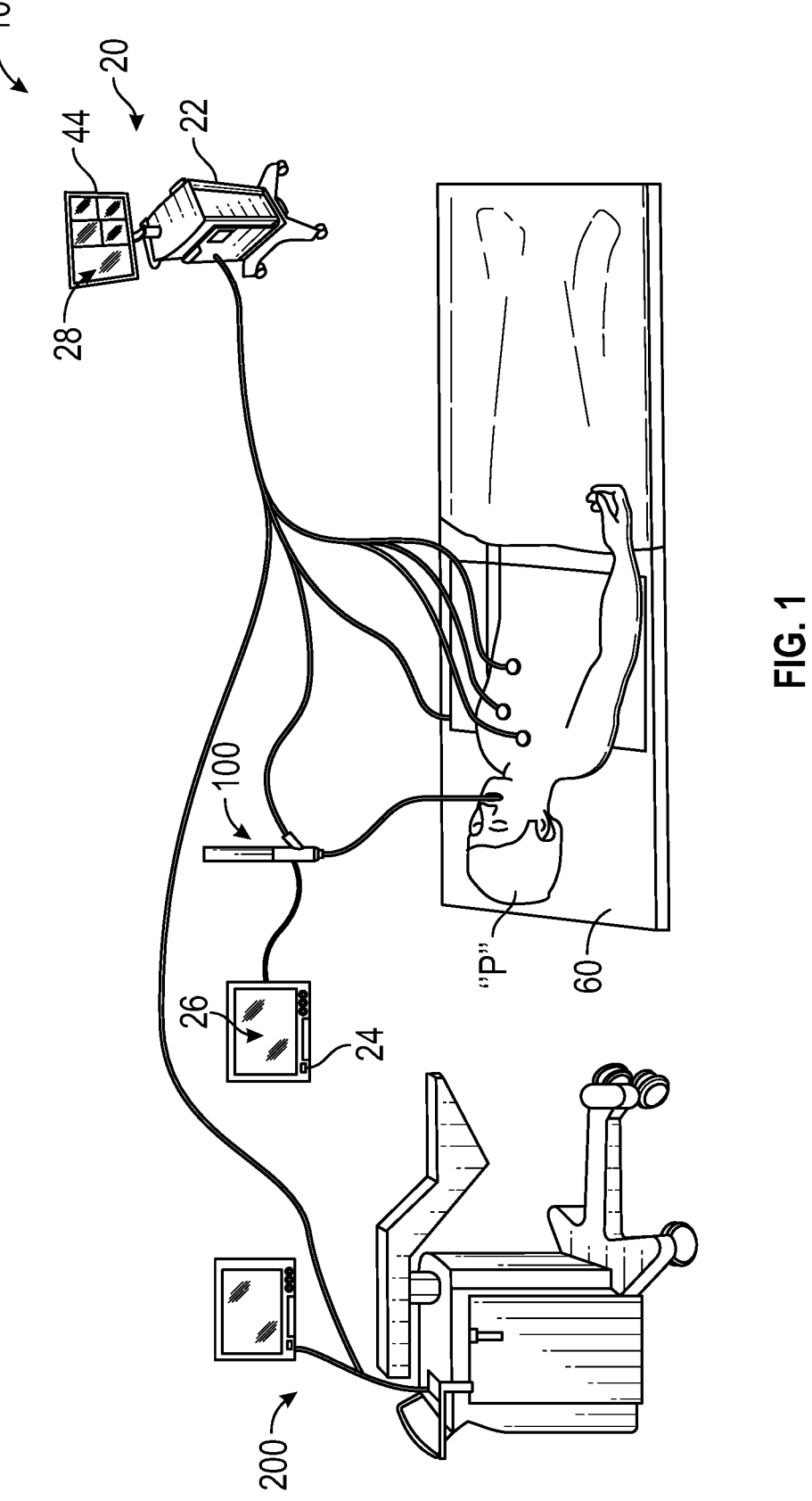
FIG. 1 is a schematic view of a surgical system provided in accordance with the present disclosure.

The present disclosure is directed to a surgical system that is configured to identify target tissue, automatically register real-time images captured by a surgical instrument to a generated 3-Dimensional (3D) model, and navigate the surgical instrument to target tissue. The surgical system generates a 3D reconstruction of a patient's airway tree, which in embodiments may be a 3D model of the patient's lungs, and identifies bifurcations, branches, or branch points. The identified branches or branch points are labeled according to their position within the patient's lungs in accordance with well accepted nomenclature, such as RB1 (right branch 1), LB1 (left branch 1), etc. and/or B1 (bifurcation 1), B2 (Bifurcation 2), etc.

The system facilitates identification of a target tissue within the 3D reconstruction and generates a pathway to the target tissue through which a surgical instrument, such as an endoscope, may be navigated. The endoscope includes a camera disposed on a distal portion thereof that is configured to capture real-time images of the patient's anatomy. The software segments or otherwise analyzes the real-time images to identify anatomical structures, such as branches or branch points. The identified branches and/or branch points are compared to the identified and labeled branches and/or branch points within the pre-procedure images and/or 3D model to identify a location within the patient's anatomy from which the real-time images were captured. Using the identified location within the patient's anatomy, the position of the endoscope from where the real-time images were taken can be registered to the 3D model, eliminating the need to register the position of the endoscope to the 3D model via electromagnetic navigation (EMN) or fluoroscopy, thereby minimizing the amount of radiation exposure to the patient and minimizing set-up time and complexity from the surgical procedure.

As the endoscope is further advanced within the airways, the real-time images captured by the camera associated with the endoscope are continually analyzed and compared to the pre-procedure or peri-procedural images and/or 3D model. If the software determines that the location from which the images were captured by the camera correspond to the pathway to the target tissue, the software permits further navigation of the endoscope within the patient's airways. If the software determines that the location from which the images were captured by the camera do not correspond to the pathway to the target tissue, the software issues a warning or alert to the user to indicate that the endoscope is no longer on the pathway to the target tissue and correction may be required. As can be appreciated, the process may be repeated as many times as necessary until it is determined that the endoscope is located adjacent the target tissue.

Although generally described with reference to the lung, it is contemplated that the systems and methods described herein may be used with any structure within the patient's body, such as the liver, kidney, prostate, gynecological, amongst others.

Turning now to the drawings, FIG. 1 illustrates a surgical system provided in accordance with the present disclosure and generally identified by reference numeral 10. As will be described in further detail hereinbelow, the surgical system 10 is generally configured to identify target tissue, automatically register real-time images captured by a surgical instrument to a generated 3-Dimensional (3D) model, and navigate the surgical instrument to the target tissue.

The surgical system includes an endoscope 100, a controller or workstation 20 operably coupled to the endoscope 100, and a robotic surgical system 200 (FIG. 10) operably coupled to the controller 20 and operably coupled to the endoscope 100. The patient "P" is shown lying on an operating table 60 with the endoscope 100 inserted through the patient's mouth and into the patient's airways, although it is contemplated that the endoscope 100 may be inserted into any suitable body cavity of the patient, depending upon the procedure being performed.

Figure 2:
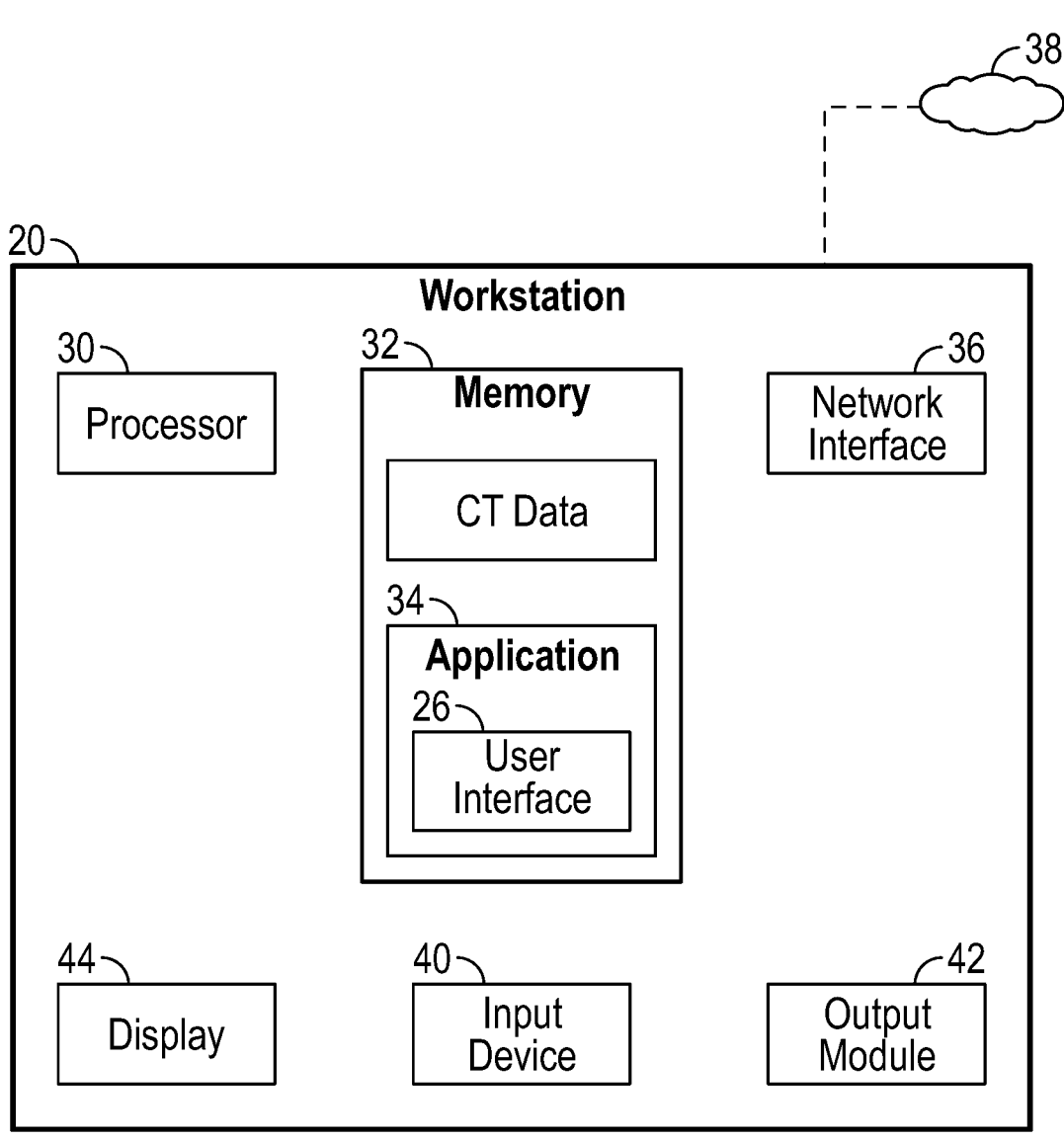
FIG. 2 is a schematic view of a controller of the surgical system of FIG. 1.

Continuing with FIG. 1 and with additional reference to FIG. 2, the controller 20 includes a computer 22 and a display 24 that is configured to display one or more user interfaces 26 and/or 28. The controller 20 may be a desktop computer or a tower configuration with the display 24 or may be a laptop computer or other computing device. The controller 20 includes a processor 30 which executes software stored in a memory 32. The memory 32 may store video or other imaging data captured by the endoscope 100 or pre-procedure images from, for example, a computer-tomography (CT) scan, Positron Emission Tomography (PET), Magnetic Resonance Imaging (MM), Cone-beam CT, amongst others. In addition, the memory 32 may store one or more applications 34 to be executed on the processor 30. Though not explicitly illustrated, the display 24 may be incorporated into a head mounted display such as an augmented reality (AR) headset such as the HoloLens offered by Microsoft Corp.

A network interface 36 enables the controller 20 to communicate with a variety of other devices and systems via the Internet. The network interface 36 may connect the controller 20 to the Internet via a wired or wireless connection. Additionally, or alternatively, the communication may be via an ad-hoc Bluetooth® or wireless network enabling communication with a wide-area network (WAN) and/or a local area network (LAN). The network interface 36 may connect to the Internet via one or more gateways, routers, and network address translation (NAT) devices. The network interface 36 may communicate with a cloud storage system 38, in which further image data and videos may be stored. The cloud storage system 38 may be remote from or on the premises of the hospital such as in a control or hospital information technology room. It is envisioned that the cloud storage system 38 could also serve as a host for more robust analysis of acquired images, etc. (e.g., additional or reinforcement data for analysis and/or comparison). An input module 40 receives inputs from an input device such as a keyboard, a mouse, voice commands, amongst others. An output module 42 connects the processor 30 and the memory 32 to a variety of output devices such as the display 24. In embodiments, the controller 20 may include its own display 44, which may be a touchscreen display.

Figure 3:
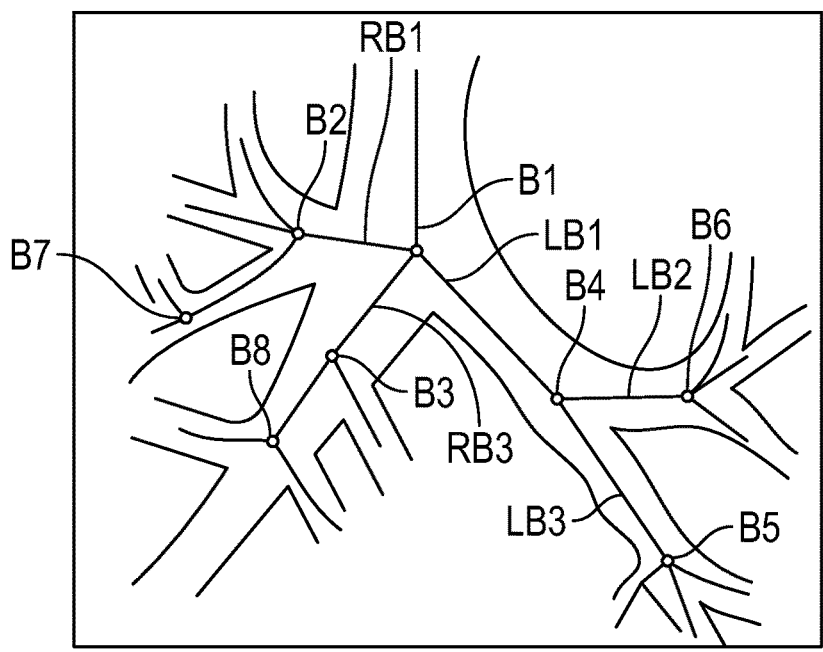
FIG. 3 is a depiction of a graphical user interface of the surgical system of FIG. 1 illustrating labels overlaid on a three-dimensional model corresponding to anatomical structures.
Figure 4:
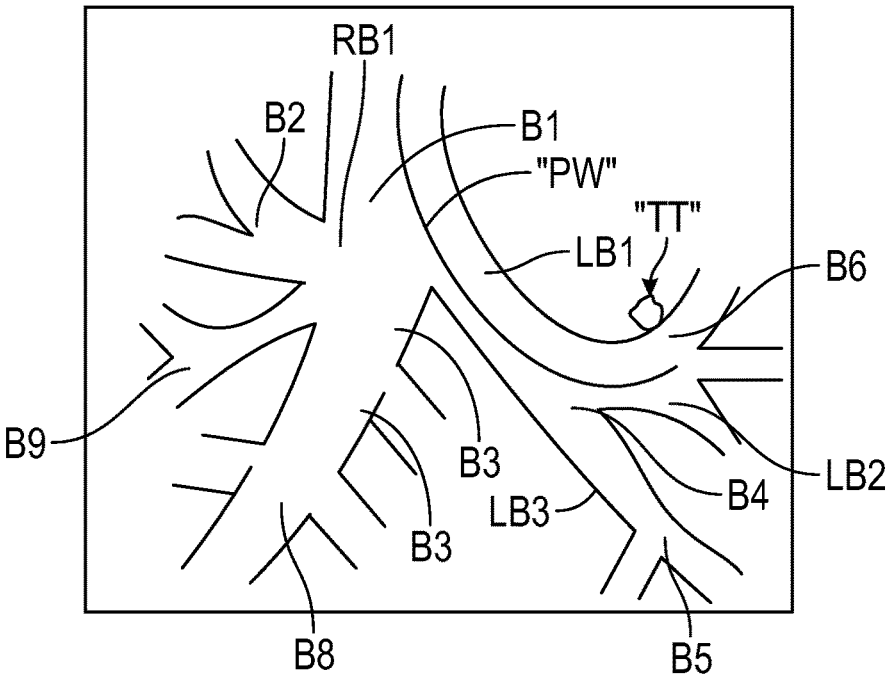
FIG. 4 is a depiction of the graphical user interface of FIG. 3 illustrating a pathway to target tissued overlaid on the three-dimensional model.

With reference to FIGS. 3 and 4, in a planning or pre-procedure phase, the software stored in the memory 32 and executed by the processor 30 utilizes acquired or pre-procedure CT image data, either stored in the memory 32 or retrieved via the network interface 36, for generating and viewing a 3D model (FIG. 3) of the patient's anatomy, enabling the identification of target tissue ("TT") on the 3D model (automatically, semi-automatically, or manually), and in embodiments, allowing for the selection of a pathway ("PW") through the patient's anatomy to the target tissue. One example of such an application is the ILLUMISITE® planning and navigation suites currently marketed by Medtronic. The 3D model may be displayed on the display 24 or another suitable display (not shown) associated with the controller 20, or in any other suitable fashion. Using the controller 20, various views of the 3D model may be provided and/or the 3D model may be manipulated to facilitate identification of target tissue on the 3D model and/or selection of a suitable pathway to the target tissue.

It is envisioned that the 3D model may be generated by segmenting and reconstructing the airways of the patient's lungs to generate a 3D airway tree. The reconstructed 3D airway tree includes various branches and bifurcations which are labeled in accordance with well accepted nomenclature, such as RB1 (right branch 1), LB1 (left branch 1), etc. and/or B1 (bifurcation 1), B2 (Bifurcation 2), etc. In embodiments, the segmentation and labeling of the airways of the patient's lungs is performed to a resolution that includes terminal bronchioles having a diameter of approximately less than 1 mm. As can be appreciated, segmenting the airways of the patient's lungs to terminal bronchioles, such as those having a diameter of approximately less than 1 mm, improves the accuracy of the pathway to the target tissue and the improves the ability of the software application to identify the location of the endoscope within the airways and navigate the endoscope 100 to the target tissue. In this manner, the use of electromagnetic navigation and/or fluoroscopy to determine the location of the endoscope 100 within the airways is minimized. Additionally, those of skill in the art will recognize that a variety of different algorithms may be employed to segment the CT image data set, including connected component, region growing, thresholding, clustering, watershed segmentation, edge detection, amongst others. It is envisioned that the entire reconstructed 3D airway tree may be labeled, or only branches or branch points within the reconstructed 3D airway tree that are located adjacent the pathway to the target tissue.

In embodiments, the software stored in the memory 32 may identify and segment out a targeted critical structure ("TT") within the 3D model. It is envisioned that the segmentation process may be performed automatically, manually, or a combination of both. The segmentation process isolates the targeted critical structure from the surrounding tissue in the 3D model and identifies its position within the 3D model. In embodiments, the software stored in the memory 32 segments the CT images to terminal bronchioles that are less than 1 mm in diameter such that branches and/or bifurcations are identified and labeled deep into the patient's luminal network. As can be appreciated, this position can be updated depending upon the view selected on the display 24 such that the view of the segmented targeted critical structure may approximate a view captured by the endoscope 100, as will be described in further detail hereinbelow.

Utilizing the position of the targeted critical structure within the 3D model and the selected pathway, the software stored on the memory 32 identifies the branch points and/or branches through which the endoscope 100 must be navigated in order to reach the targeted critical tissue. As such, images associated with these labeled branch points are identified and compared to real-time images captured by the endoscope 100 to identify a position of the endoscope 100 within the patient's airways, as will be described in further detail hereinbelow. In embodiments, the software stored on the memory 32 may create a table including the labeled branches or branch points and their locations within the 3D model or the 3D model may include the labels displayed on all or a portion thereof.

Figure 5:
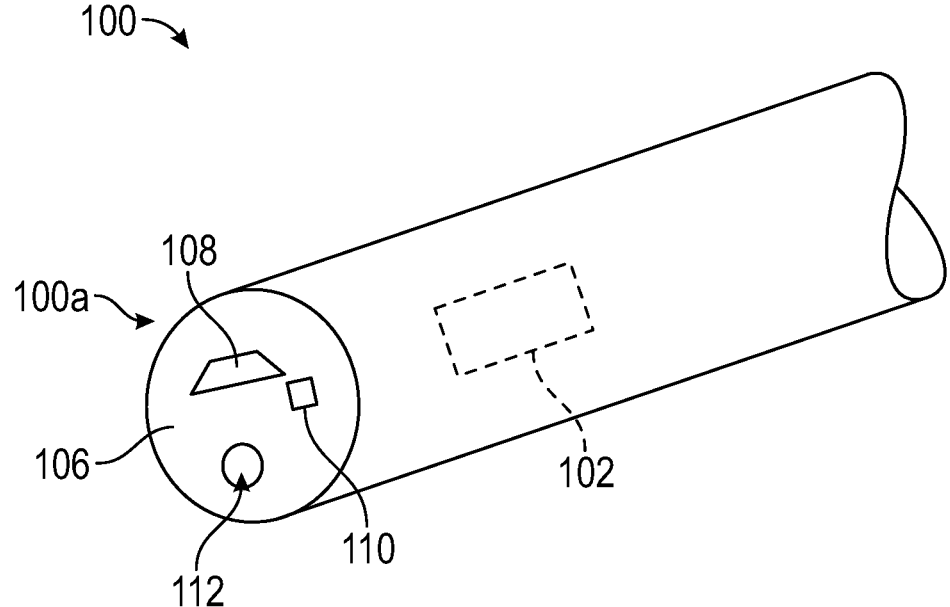
FIG. 5 is a perspective view of a distal end portion of an endoscope of the surgical system of FIG. 1.

Turning to FIG. 5, the endoscope 100 having a distal end portion 100a is illustrated and includes a distal surface 106 adjacent the distal end portion having a camera 108 disposed thereon. Although generally illustrated as having one camera 108, it is contemplated that the endoscope 100 may include any number of cameras disposed on the distal surface 106 or any other suitable location thereon (e.g., sidewall, etc.). It is envisioned that the camera 108 is a complementary metal-oxide-semiconductor (CMOS) camera, and in embodiments, may be a mini-CMOS camera. In other aspects, the camera 108 may also be disposed external to the endoscope 100 and operably coupled to the distal end portion 10a of the endoscope via an optical fiber (not shown) or the like. As can be appreciated, the camera 108 captures images of the patient's anatomy from a perspective of looking out from the distal surface 106. Although generally identified as being a CMOS camera, it is envisioned that the camera 108 may be any suitable camera, such as charge-coupled device (CCD), complementary metal-oxide-semiconductor (CMOS), N-type metal-oxide-semiconductor (NMOS), and in embodiments, may be a white light camera, infrared (IR) camera, amongst others, depending upon the design needs of the system 10.

In embodiments, the endoscope 100 may include one or more light sources 110 disposed on the distal surface 106 or any other suitable location (e.g., side surface, protuberance, etc.). The light source 110 may be or may include a light emitting diode (LED), an optical fiber connected to a light source that is located external to the patient, amongst others, and may emit white, IR, or near infrared (NIR) light. In this manner, the camera 108 may be a white light camera, IR camera, or NIR camera, a camera that is capable of capturing white light and NIR light, amongst others. In one non-limiting embodiment, the camera 108 is a white light mini-CMOS camera.

The endoscope 100 includes one or more working channels 112 defined therethrough and extending through the distal surface 106. The working channel 112 is configured to receive a tool (not shown), locatable guide (LG), amongst others to enable a clinician to navigate to, or treat, target tissue. It is contemplated that the tool may be any suitable tool utilized during an endoscopic surgical procedure, and in embodiments, may be a fixed tool.

Figure 6:
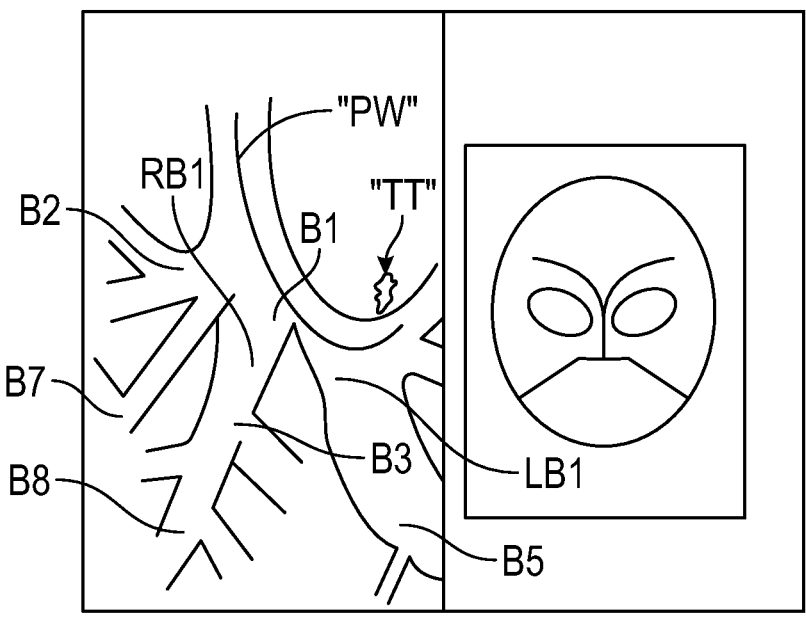
FIG. 6 is a depiction of the graphical user interface of FIG. 3 illustrating a three-dimensional model with labels overlaid thereon adjacent to real-time images captured by the endoscope of FIG. 5.
Figure 7:
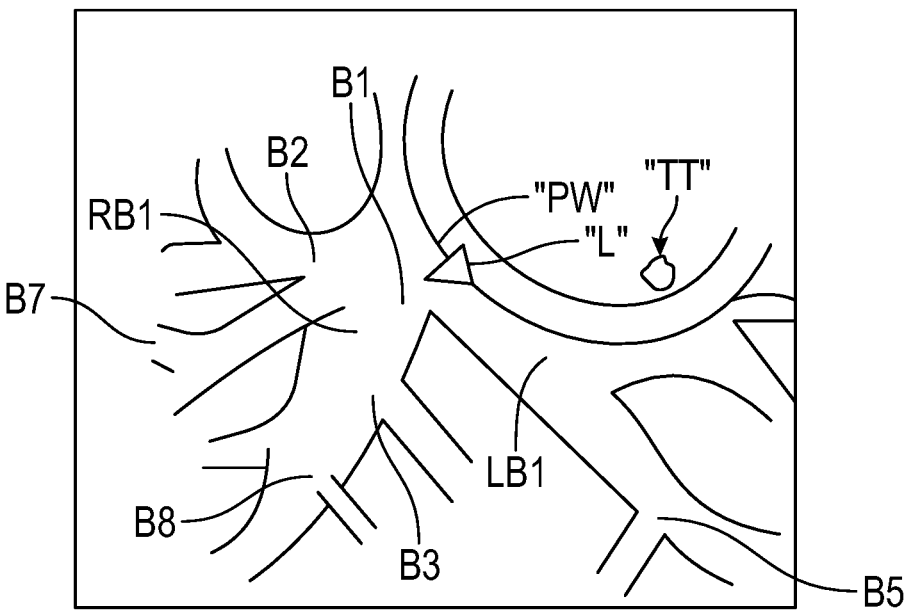
FIG. 7 is depiction of the graphical user interface of FIG. 3 illustrating a depiction of a location of the endoscope of FIG. 5 within the patient's lungs overlaid on the three-dimensional model.

With reference to FIGS. 6 and 7, the software stored in the memory 32 communicates with the camera 108 to capture images in real-time of the patient's anatomy as the endoscope 100 is navigated through the luminal network of the patient. The real-time images captured by the camera 108 are compared to the pre-procedure images to identify commonalities between the branches and bifurcations identified by the software in the real-time images captured by the camera and the pre-procedure images. In this manner, as the endoscope 100 is initially advanced within the patient's airways, the camera 108 captures images of the first bifurcation of the trachea into the left and right bronchus, which may be labeled as B1, LB1, and RB1, respectively in the pre-procedure images or 3D reconstruction of the airway tree. Using the pre-procedure images and/or 3D model labeled by the software during the planning or pre-procedure phase, the software stored on the memory 32 identifies pre-procedure images that correspond to the real-time images captured by the camera 108 via the identified and labeled branches or branch points. In this manner, the software stored on the memory 32 associates the branches or branch points identified in the real-time images with the labeled branches or bifurcations B1, LB1, and RB1, etc. In this manner, the position of the endoscope 100 within the patient's airway is identified and registered to the 3D model and displayed to the user via a marker "L" overlaid on the 3D model.

Although generally described as utilizing pre-procedure images, it is envisioned that the labeled branches or bifurcations may be continuously updated based on intraprocedural images captured perioperatively. As can be appreciated, by updating the images utilized to identify the branches or bifurcations and the labeling thereof, the 3D model can more accurately reflect the real time condition of the lungs, taking into account atelectasis, mechanical deformation of the airways, etc. Although generally described with respect to the airways of a patient's lungs, it is envisioned that the software stored in the memory 32 may label portions of the bronchial and/or pulmonary circulatory system within the lung. These labels may appear concurrently with the labels of branches or bifurcations of the airways displayed to the user.

In embodiments, the real-time images captured by the camera 108 are segmented via the software stored in the memory 32 to identify structures and/or lumens (e.g., airways) within the real-time images. With the structures and/or lumens identified within the real-time images, the software stored on the memory 32 compares the segmented real-time images to the labeled pre-procedure images and/or 3D model and matches the bifurcations and/or branches to those labeled in the pre-procedure images and/or 3D model to identify a position within the patient's airways from which the real-time images were captured by the camera 108, and therefore, a location of the endoscope 100 within the patient's airways. As can be appreciated, identifying the location of the endoscope 100 by comparing the segmented real-time images to the pre-procedure images and/or 3D model, registration of the position of the endoscope 100 can be initially, and continuously performed as the endoscope 100 is advanced within the patient's airways, minimizing the need to utilize fluoroscopy or other modalities to identify the position of the endoscope within the patient's airways.

By comparing the real-time images captured by the camera 108 to the labeled pre-procedure images and/or 3D model, registration of the location of the endoscope 100 within the airways of the patient's lungs can be performed without the aid of electromagnetic navigation (EMN) or Fluoroscopy, minimizing the number of systems and/or components necessary to perform the procedure and reducing patient radiation exposure. While generally described as not utilizing EMN or fluoroscopy during the procedure to identify the location of the endoscope 100 within the airways of the patient's lungs, it is contemplated that EMN or fluoroscopy may be utilized in certain instances to confirm the location of the endoscope 100 within the airways, such as initial registration or to confirm that the endoscope 100 is located adjacent the target tissue before performing a biopsy or other treatment, amongst others.

As the endoscope 100 is navigated through the airways of the patient, the real-time images captured by the camera 108 are continuously segmented and compared against the pre-procedure images and/or 3D model to identify each branch point or branch labeled in the pre-procedure images and/or 3D model. When a branch or branch point is identified in the real-time images captured by the camera 108, the branch or branch point identified within the real-time images is com-pared against the labeled pre-procedure images and/or 3D model to identify the labeled branch or branch point to which the branch or branch point identified within the real-time images corresponds. In this manner, if the branch or branch point identified within the real-time images cor-responds to a labeled branch or branch point within the pre-procedure images and/or 3D model along the pathway to the target tissue, the software stored in the memory 32 registers or otherwise confirms the location of the endoscope 100 within the airways of the patient. In contrast, if the branch or branch point identified within the real-time images does not correspond to a labeled branch or branch point within the pre-procedure images and/or 3D model that is along the pathway to the target tissue, the software stored on the memory 32 issues a warning or note that the endoscope 100 may no longer be located on the pathway to the target tissue and retraction of the endoscope 100 to a labeled branch or branch point within the pre-procedure and/or 3D model along the pathway to the target tissue may be required. In embodiments, if the location of the endoscope 100 within the airways of the patient cannot be identified by comparing the real-time images captured by the camera 108 to the pre-procedure and/or 3D model, EMN or fluoroscopy may be employed to identify the real-time position of the endoscope 100.

Figure 8A:
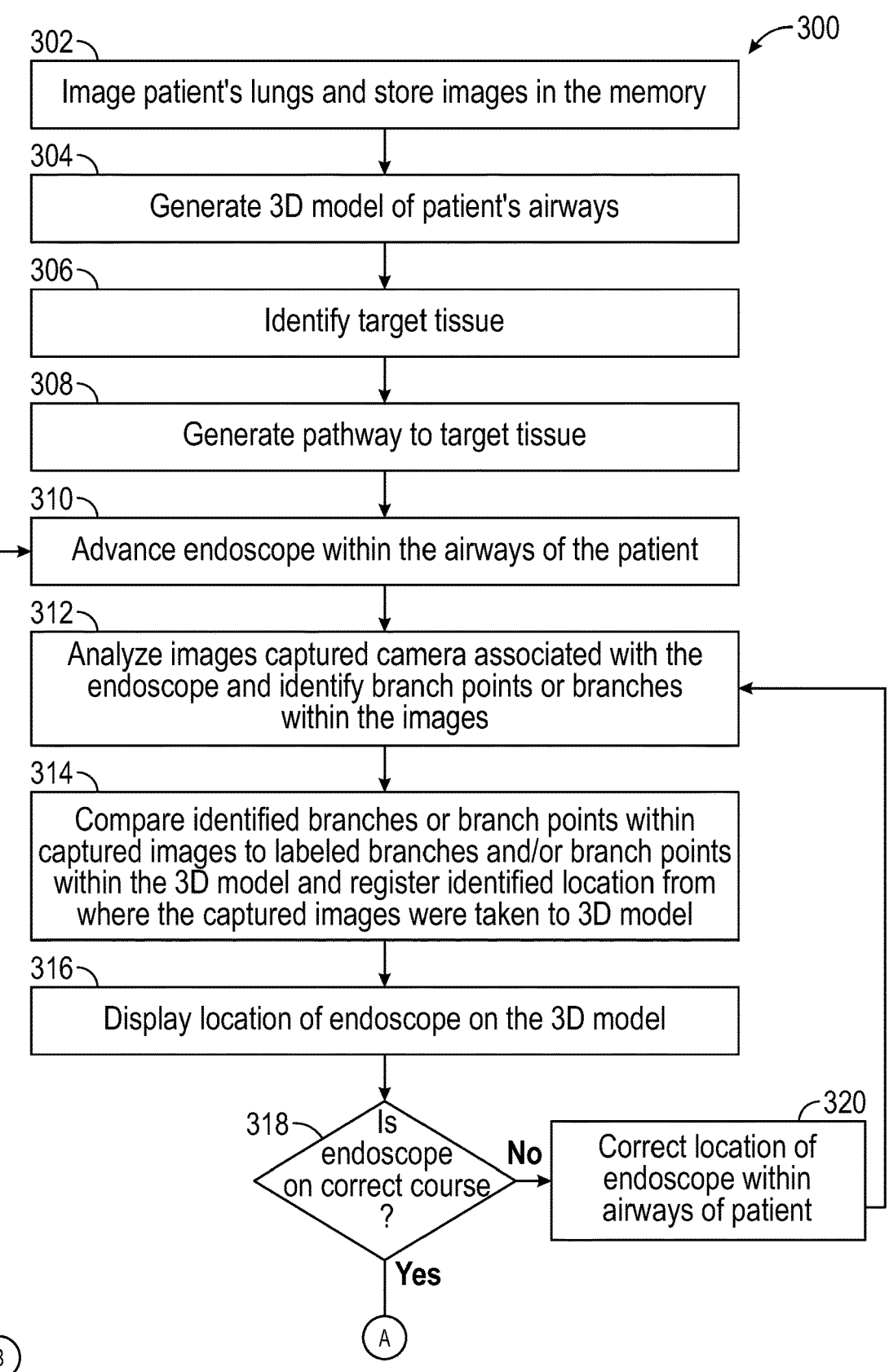
FIG. 8A is a flow diagram of a method of navigating a surgical instrument to target tissue in accordance with the present disclosure.
Figure 8B:
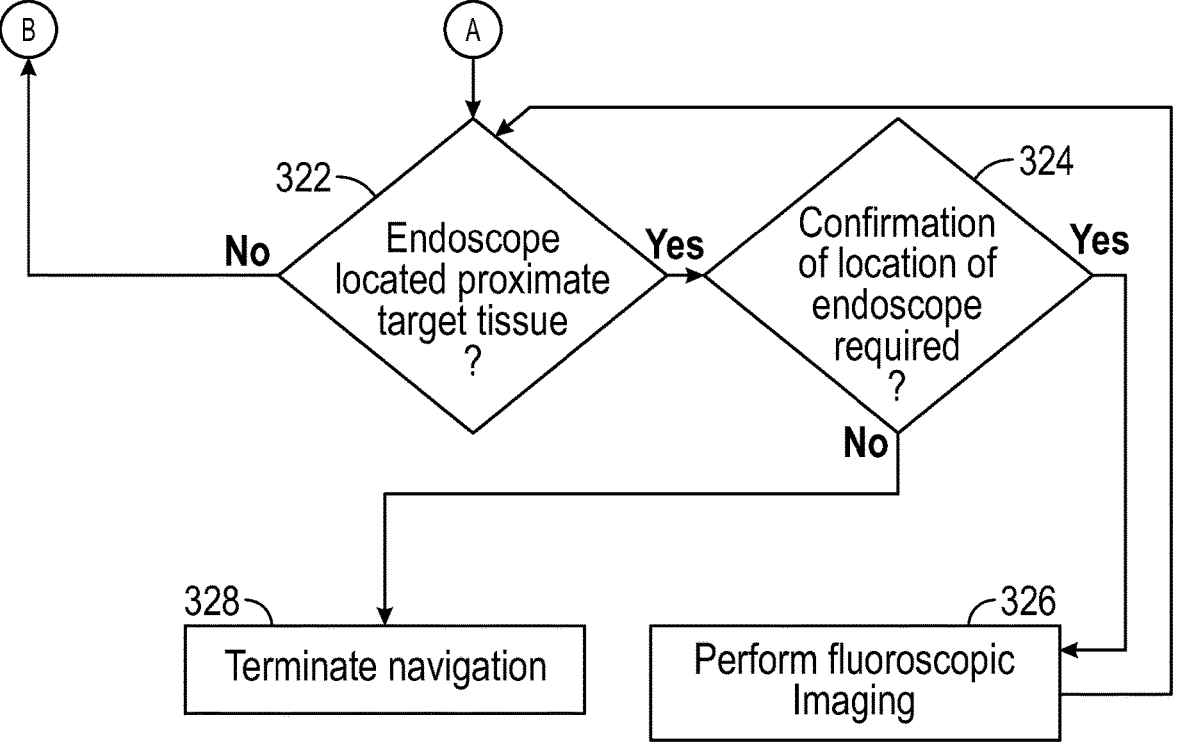
FIG. 8B is a continuation of the flow diagram of FIG. 8A

With reference to FIGS. 8A and 8B, a method of navi-gating an endoscope through a luminal network of a patient's lungs to a target tissue is described and generally identified by reference numeral 300. Initially, in step 302, the patient's lungs are imaged using any suitable imaging modality (e.g., CT, MM, amongst others) and the images are stored on the memory 32 associated with the controller 20. In step 304, the images stored on the memory 32 are utilized to generate and view a 3D reconstruction of the airways of the patient's lungs, and thereafter, target tissue is identified in step 306. Thereafter, branches or branch points within the 3D reconstruction are identified and labeled in step 308. With the target tissue identified and branches and/or branch-points within the 3D reconstruction labeled, a pathway to the target tissue through the luminal network of the patient's lungs is generated in step 308.

Once the desired pathway to the target tissue is selected, the surgical procedure is initiated in step 310 by advancing the distal end portion 100a of the endoscope 100 within the airways of the patient's lungs. With the distal end portion 100a of the endoscope 100 disposed within the airways of the patient's lungs, in step 312, real-time images are cap-tured by the camera 108 of the endoscope 100 and seg-mented to identify branches and/or branch points within the captured real-time images. In step 314, the branches and/or branch points identified within the captured real-time images are compared to the labeled branches and/or branch points of the 3D reconstruction and once a match is identified, the location of the distal end portion 100a of the endoscope 100 is identified and registered to the 3D reconstruction. With the position of the distal end portion 100a of the endoscope 100 registered to the 3D reconstruction, the position of the distal end portion 100a of the endoscope 100 within the 3D reconstruction is displayed on the 3D reconstruction in step 316.

The real-time images captured by the camera 108 are continuously analyzed by the software stored on the memory 32 as the endoscope 100 is further advanced within the airways of the patient's lungs and compared to the labeled branches and/or branch points within the pre-procedure images and/or 3D reconstruction. In step 318, the software application determines if the distal end portion 100a of the endoscope is on the correct course (e.g., along the pathway to the target tissue) by comparing the branches and/or branch points identified within the real-time images captured by the camera 108 and determining if the identified branches and/or branch points within the real-time images correspond to labeled branches and/or branch points within the pre-proce-dure images and/or 3D reconstruction along the pathway to the target tissue. If the branches and/or branch points iden-tified within the real-time images captured by the camera 108 do not correspond to the labeled branches and/or branch points within the pre-procedure images and/or 3D recon-struction along the pathway to the target tissue, in step 320, the software stored on the memory 32 issues a warning, an alert, or other message (e.g., audible, text, flashing, amongst others) to the clinician that the position of the distal end portion 100a of the endoscope 100 is no longer on the pathway to the target tissue and that a correction to the path of the endoscope 100 may be required.

Once the position of the distal end portion 100a of the endoscope 100 has been altered, the method returns to step 312 and navigation of the endoscope through the airways of the patient is continued. If, in step 318, the branches and/or branch points identified within the real-time images captured by the camera 108 do correspond to the labeled branches and/or branch points within the pre-procedure images and/or 3D reconstruction along the pathway to the target tissue, in step 322, it is determined if the distal end portion 100a of the endoscope 100 is located adjacent the target tissue. If it is determined that the distal end portion 100a of the endoscope 100 is not located adjacent the target tissue, the method returns to step 312. If it is determined that the distal end portion 100a of the endoscope 100 is located adjacent the target tissue, it is determined if confirmation of the position of the distal end portion 100a of the endoscope 100 relative to the target tissue may be required in step 324.

If confirmation of the position of the distal end portion 100a of the endoscope 100 relative to the target tissue is required, in step 326, fluoroscopic imaging or any other suitable imaging modality may be performed, and thereafter, the method returns to step 322. If confirmation of the location of the distal end portion 100a of the endoscope 100 is not required, the target tissue is treated in step 328. If the fluoroscopic imaging indicates that the distal end portion 100a of the endoscope 100 is not located adjacent the target tissue, the method returns to step 312.

Figure 9:
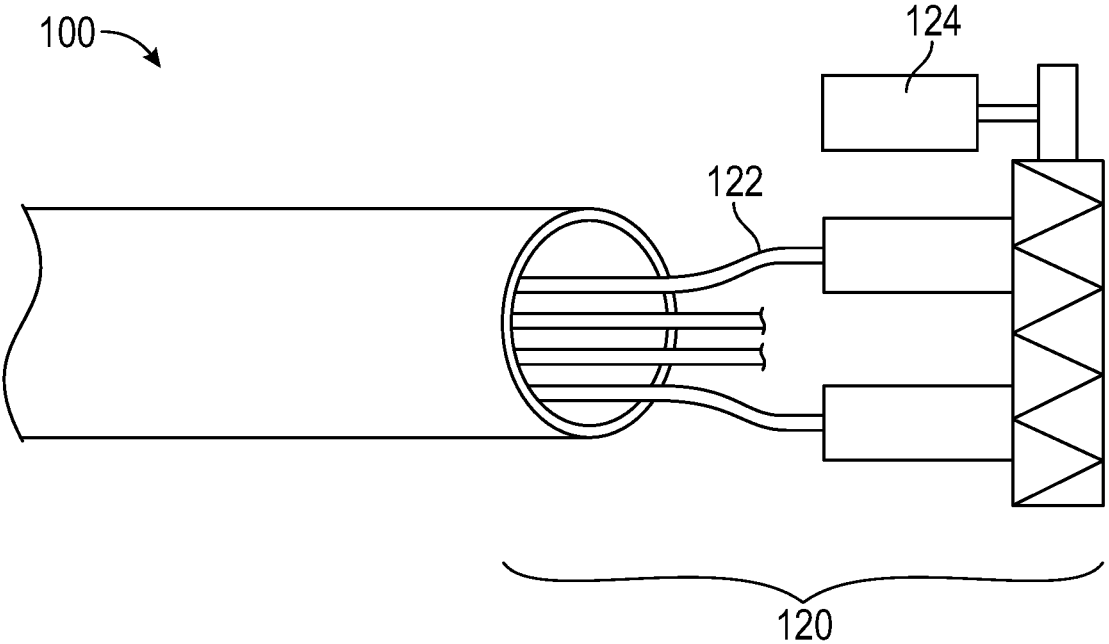
FIG. 9 is an exploded view of a drive mechanism of the endoscope of FIG. 5.

Turning to FIG. 9, it is envisioned that the endoscope 100 may include a drive mechanism 120 disposed within an interior portion thereof that is operably coupled to a proxi-mal portion of the endoscope 100. The drive mechanism 120 effectuates manipulation or articulation of a distal portion 100a of the endoscope 100 in four degrees of freedom (e.g., left, right, up, down), which is controlled by two push-pull wires, although it is contemplated that the drive mechanism 120 may include any suitable number of wires to effectuate movement and/or articulation of the distal portion 100a of the endoscope 100 in greater or fewer degrees of freedom without departing from the scope of the present disclosure. It is envisioned that the drive mechanism 120 may be cable actuated using artificial tendons or pull wires 122 (e.g., metallic, non-metallic, composite, etc.) or may be a nitinol wire mechanism. In embodiments, the drive mechanism 120 may include motors 124 or other suitable devices capable of effectuating movement of the pull wires 122. In this manner, the motors 124 are disposed within the endoscope 100 such that rotation of the motors 124 effectuates a corresponding articulation of the distal portion 100a of the endoscope 100.

Figure 10:
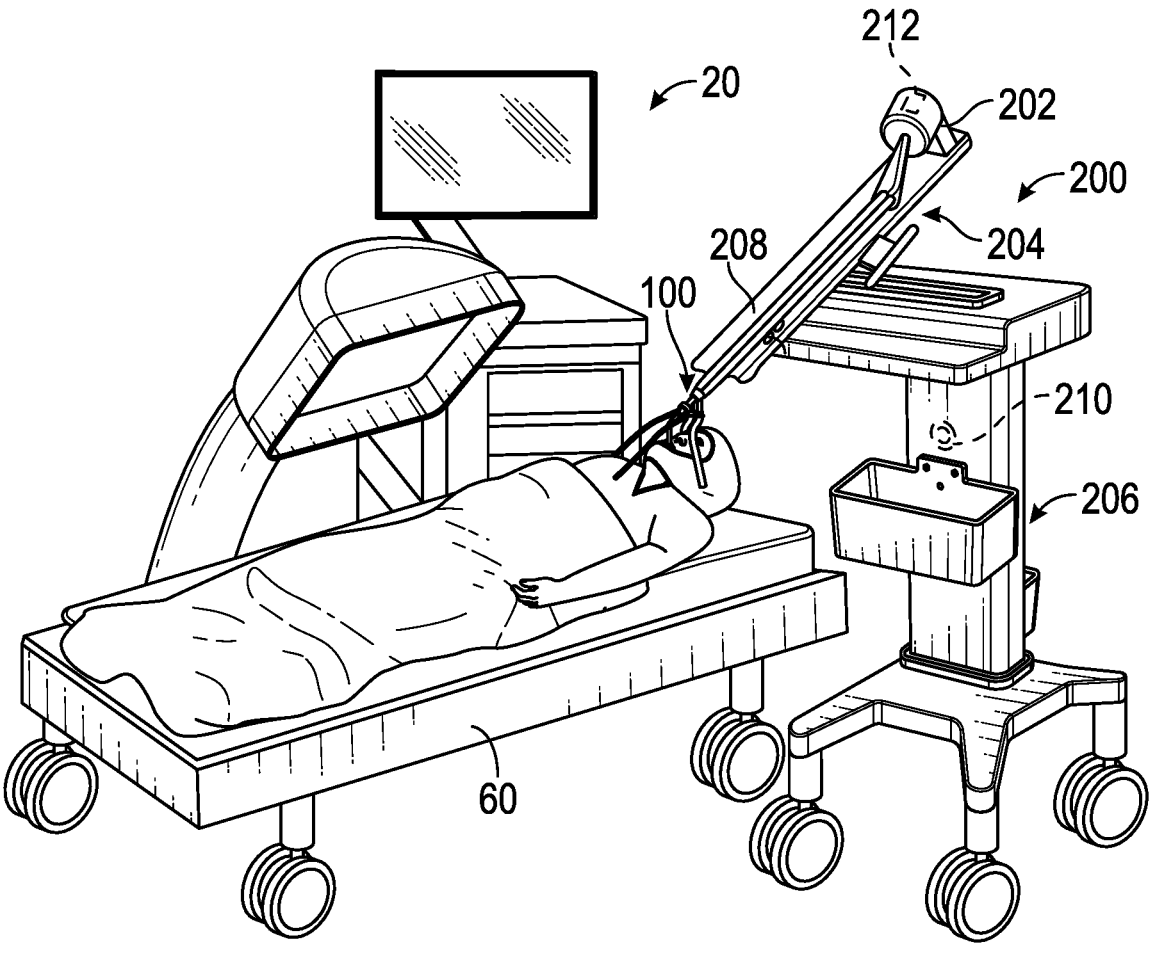
FIG. 10 is a perspective view of a robotic surgical system of the surgical system of FIG. 1.

Turning to FIG. 10, the system 10 includes a robotic surgical system 200 that is operably coupled to the endoscope 100. The robotic surgical system 200 includes a drive mechanism 202 including a robotic arm 204 operably coupled to a base or cart 206. The robotic arm 204 includes a cradle 208 that is configured to receive a portion of the endoscope 100 thereon. The endoscope 100 is coupled to the cradle 208 using any suitable means (e.g., straps, mechanical fasteners, couplings, amongst others).

It is envisioned that the robotic surgical system 200 may communicate with the endoscope 100 via electrical connection (e.g., contacts, plugs, etc.) or may be in wireless communication with the endoscope 100 to control or otherwise effectuate movement of the motors 124 and receive images captured by the camera 108. In this manner, it is contemplated that the robotic surgical system 200 may include a wireless communication system 210 operably coupled thereto such that the endoscope 100 may wirelessly communicate with the robotic surgical system 200 and/or the controller 20 via Wi-Fi, Bluetooth®, amongst others. As can be appreciated, the robotic surgical system 200 may omit the electrical contacts altogether and may communicate with the endoscope 100 wirelessly or may utilize both electrical contacts and wireless communication. The wireless communication system 210 is substantially similar to the wireless network interface 28 of the controller 20, and therefore, the wireless communication system 210 will not be described in detail herein in the interest of brevity. In embodiments, the robotic surgical system 200 and the controller 20 may be one in the same or may be widely distributed over multiple locations within the operating room. It is contemplated that the controller 20 may be disposed in a separate location and the display 12 may be an overhead monitor disposed within the operating room.

Although generally described as having the motors 124 disposed within the endoscope 100, it is contemplated that the endoscope 100 may not include motors 124 disposed therein. In this manner, the drive mechanism 120 disposed within the endoscope 100 may interface with motors 124 disposed within the cradle 208 of the robotic surgical system 200. In embodiments, the endoscope 100 may include a motor or motors 124 for controlling articulation of the distal end portion 100a of the endoscope in one plane (e.g., left/null, right/null, etc.) and the drive mechanism 202 of the robotic surgical system 200 may include at least one motor 212 to effectuate the second axis of rotation and for axial motion. In this manner, the motor 124 of the endoscope 100 and the motors 212 of the robotic surgical system 200 cooperate to effectuate four-way articulation of the distal end portion 100a of the endoscope 100 and effectuate rotation of the endoscope 100. As can be appreciated, by removing the motors 124 from the endoscope 100, the endoscope 100 becomes increasingly cheaper to manufacture and may be a disposable unit. In embodiments, the endoscope 100 may be integrated into the robotic surgical system 200 (e.g., one piece) and may not be a separate component.

Although described generally hereinabove, it is envisioned that the memory 32 may include any non-transitory computer-readable storage media for storing data and/or software including instructions that are executable by the processor 30 and which control the operation of the controller 20 and, in some embodiments, may also control the operation of the endoscope 100. In an embodiment, memory 32 may include one or more storage devices such as solid-state storage devices, e.g., flash memory chips. Alternatively, or in addition to the one or more solid-state storage devices, the memory 32 may include one or more mass storage devices connected to the processor 30 through a mass storage controller (not shown) and a communications bus (not shown).

Although the description of computer-readable media contained herein refers to solid-state storage, it should be appreciated by those skilled in the art that computer-readable storage media can be any available media that can be accessed by the processor 30. That is, computer readable storage media may include non-transitory, volatile and non-volatile, removable and non-removable media implemented in any method or technology for storage of information such as computer-readable instructions, data structures, program modules or other data. For example, computer-readable storage media may include RAM, ROM, EPROM, EEPROM, flash memory or other solid-state memory technology, CD-ROM, DVD, Blu-Ray or other optical storage, magnetic cassettes, magnetic tape, magnetic disk storage or other magnetic storage devices, or any other medium which may be used to store the desired information, and which may be accessed by the controller 20.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of embodiments. Those skilled in the art will envision other modifications within the scope and spirit of the claims appended hereto.

What is claimed is:

1. A system for performing a surgical procedure, comprising:

a controller operably coupled to a camera, the controller including a memory and a processor, the memory storing instructions, which when executed by the processor cause the processor to:

receive a plurality of pre-procedure images of a patient's anatomy;

label anatomical bifurcations within at least a portion of the pre-procedure images;

generate a three-dimensional reconstruction of the patient's anatomy using the plurality of pre-procedure images;

receive an image captured by the camera;

identify anatomical bifurcations within the image captured by the camera;

compare the identified anatomical bifurcations within the image captured by the camera to labeled anatomical bifurcations within the plurality of pre-procedure images;

identify an image from the plurality of pre-procedure images that corresponds to the image captured by the camera;

register a location where the image was captured by the camera to the three-dimensional reconstruction of the patient's anatomy;

display a representation of at least a portion of the camera in the three-dimensional reconstruction at the location where the image was captured;

receive intraprocedural images from a second, external imaging modality; and receive, based on the intraprocedural images, confirmation that the displayed location of the representation of the camera in the three-dimensional reconstruction relative to target tissue is accurate.

2. The system according to claim 1, further comprising a surgical device, wherein the camera is disposed on a distal portion of the surgical device, wherein the surgical device is navigable within a portion of the patient's anatomy.

3. The system according to claim 1, wherein the instructions, when executed by the processor, cause the processor to generate a pathway to the target tissue.

4. The system according to claim 3, wherein the instructions, when executed by the processor, cause the processor to label anatomical bifurcations adjacent the pathway to the target tissue.

5. The system according to claim 3, wherein the instructions, when executed by the processor, cause the processor to confirm that the images captured by the camera were captured from a location within the patient's anatomy that corresponds to the pathway to the target tissue.

6. The system according to claim 3, wherein the instructions, when executed by the processor, cause the processor to issue a warning if the images captured by the camera were captured from a location within the patient's anatomy that does not correspond to the pathway to the target tissue.

7. The system according to claim 1, wherein the instructions, when executed by the processor, cause the processor to continuously receive images from the camera and continuously register the images captured by the camera to the three-dimensional reconstruction of the patient's anatomy as a surgical device is navigated through the patient's anatomy.

8. The system according to claim 7, wherein the instructions, when executed by the processor, cause the processor to label branches of an anatomical structure within at least a portion of the pre-procedure images.

9. The system according to claim 8, wherein the instructions, when executed by the processor, cause the processor to:

display in a user interface the three-dimensional reconstruction with the labels overlaid at the bifurcations and branches, and the image captured by the camera at the registered location.

10. A system for performing a surgical procedure, comprising:

an endoscope including a camera, the camera disposed on a distal portion of the endoscope; and a controller operably coupled to the camera, the controller including a memory and a processor, the memory storing instructions, which when executed by the processor cause the processor to:

generate a three-dimensional reconstruction of a patient's anatomy from pre-procedure images of the patient's anatomy;

generate a pathway to a target tissue within the patient's anatomy;

label anatomical bifurcations along the pathway to the target tissue;

receive an image captured by the camera;

identify anatomical bifurcations within the image captured by the camera;

compare the identified anatomical bifurcations within the image captured by the camera to the labeled anatomical bifurcations within the three-dimensional reconstruction of the patient's anatomy;

identify a location within the three-dimensional reconstruction of the patient's anatomy that corresponds to the image captured by the camera;

register the location where the image was captured by the camera to the three-dimensional reconstruction of the patient's anatomy;

display a representation of at least a portion of the endoscope in the three-dimensional reconstruction at the location where the image was captured;

receive intraprocedural images from an external imaging modality; and receive, based on the intraprocedural images, confirmation that the displayed location of the representation of the endoscope in the three-dimensional reconstruction relative to the target tissue is accurate.

11. The system according to claim 10, wherein the instructions, when executed by the processor, cause the processor to confirm that the image captured by the camera was captured from a location within the patient's anatomy that corresponds to the pathway to the target tissue.

12. The system according to claim 10, wherein the instructions, when executed by the processor, cause the processor to issue a warning that the image captured by the camera was captured from a location within the patient's anatomy that does not correspond to the pathway to the target tissue.

13. The system according to claim 10, wherein the instructions, when executed by the processor, cause the processor to continuously receive images captured by the camera and continuously register the images captured by the camera to the three-dimensional reconstruction of the patient's anatomy as the endoscope is navigated through the patient's anatomy.

14. The system according to claim 10, wherein the instructions, when executed by the processor, cause the processor to:

display in a user interface the three-dimensional reconstruction with the labels overlaid at the bifurcations and branches, and the image captured by the camera at the registered location.

15. A method of performing a surgical procedure, comprising:

receiving a plurality of pre-procedure images of a patient's anatomy;

labeling anatomical bifurcations within at least a portion of the pre-procedure images;

generating a three-dimensional reconstruction of the patient's anatomy using the plurality of pre-procedure images;

receiving an image captured by a camera;

identifying anatomical bifurcations within the image captured by the camera;

comparing the identified anatomical bifurcation within the image captured by the camera to labeled anatomical bifurcation structures within the plurality of pre-procedure images;

identifying an image from the plurality of pre-procedure images that corresponds to the image captured by the camera;

registering a location where the image was captured by the camera to the three-dimensional reconstruction of the patient's anatomy;

displaying a representation of at least a portion of the camera in the three-dimensional reconstruction at the location where the image was captured;

receiving intraprocedural images from an external imaging modality; and receiving, based on the intraprocedural images, confirmation that the displayed location of the representation of the camera in the three-dimensional reconstruction relative to target tissue is accurate.

16. The method according to claim 15, wherein receiving the image captured by the camera includes receiving images captured by the camera disposed on a distal portion of a surgical device, wherein the surgical device is navigable within a portion of the patient's anatomy.

17. The method according to claim 15, further comprising generating a pathway to the target tissue located within the patient's anatomy.

18. The method according to claim 17, further comprising labeling anatomical bifurcations adjacent the pathway to the target tissue.

19. The method according to claim 17, further comprising confirming that the images captured by the camera were captured from a location within the patient's anatomy that corresponds to the pathway to the target tissue.

20. The method according to claim 17, further comprising issuing a warning if the images captured by the camera were captured from a location within the patient's anatomy that does not correspond to the pathway to the target tissue.

\* \* \* \* \*